(12) United States Patent
Hsu et al.

(10) Patent No.: US 9,375,406 B2
(45) Date of Patent: *Jun. 28, 2016

(54) SUBSTITUTED PYRIMIDINES FOR MOBILIZING CELLS EXPRESSING A TYPE 4 CXC CHEMOKINE RECEPTOR

(71) Applicant: TaiGen Biotechnology Co., Ltd., Taipei (TW)

(72) Inventors: Ming-Chu Hsu, Glendora, CA (US); Ying-Huey Huang, Taipei (TW); Chi-Feng Yen, New Taipei (TW); Chi-Hsin Richard King, Des Peres, MO (US)

(73) Assignee: Taigen Biotechnology Co., Ltd., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/502,144

(22) Filed: Sep. 30, 2014

(65) Prior Publication Data

US 2016/0090394 A1 Mar. 31, 2016

(51) Int. Cl.
| | |
|---|---|
| *C07D 239/50* | (2006.01) |
| *C07D 295/04* | (2006.01) |
| *A61K 31/00* | (2006.01) |
| *C07F 9/6558* | (2006.01) |
| *C07F 9/6561* | (2006.01) |

(52) U.S. Cl.
CPC ............... *A61K 31/00* (2013.01); *C07F 9/6561* (2013.01); *C07F 9/65583* (2013.01)

(58) Field of Classification Search
CPC ............................. C07D 239/50; C07D 295/04
USPC .................................................. 544/323, 359
See application file for complete search history.

(56) References Cited

U.S. PATENT DOCUMENTS 8,372,849 B2 * 2/2013 Yen et al. .................. 514/256

OTHER PUBLICATIONS

Wjakowski et al "Mobilization of Bone Marrow-Derived Progenitor Cells in Acute Coronary Syndromes" Folia Histochemica et Cytobiologica vol. 43, pp. 229-232. 2005.

Morimoto et al "Bone Marrow-Derived CXCR4+ Cells Mobilized by Macrophage Colony-Stimulating Factor Participate in the Reduction of Infarct Area and Improvement of Cardiac Remodeling After Myocardial Infarction in Mice" American Journal of Pathology vol. 171, pp. 755-766. 2007.
Cheng et al "Targeted Migration of Mesenchymal Stem Cells Modified with CXCR4 Gene to Infarcted Myocardium Improves Cardiac Performance" Molecular Therapy vol. 16, pp. 571-579. 2008.
Nervi et al "Chemosensitization of Acute Myeloid Leukemia (AML) Following Mobilization by the CXCR4 Antagonist AMD3100" Blood vol. 113, pp. 6206-6214. 2009.
Liekens et al "CXCL12-CXCR4 Axis in Angiogenesis, Metastasis and Stem Cell Mobilization" Current Pharmaceutical Design vol. 16, pp. 3903-3920. 2010.
Jujo et al "CXCR4 Blockade Augments Bone Marrow Progenitor Cell Recruitment to the Neovasculature and Reduces Mortality After Myocardial Infarction" Proceedings of the National Academy of Sciences vol. 107, pp. 11008-11013. 2010.
Williams et al "Enhanced Effect of Human Cardiac Stem Cells and Bone Marrow Mesenchymal Stem Cells to Reduce Infarct Size and Restore Cardiac Function After Myocardial Infarction" Circulation vol. 127, pp. 213-223. 2013.
Hsu et al "CXCR4 Antagonist TG-0054 Mobilizes Mesenchymal Stem Cells, Attenuates Inflammation, and Preserves Cardiac Systolic Function in a Porcine Model of Myocardial Infarction" Cell Transplantation. 2014.

* cited by examiner

*Primary Examiner* — Douglas M Willis
(74) *Attorney, Agent, or Firm* — Cesari and McKenna LLP

(57) ABSTRACT

A method of mobilizing cells expressing the type 4 CXC chemokine receptor into the peripheral circulation by contacting them with an effective amount of a compound of formula (I) shown below (each variable in the formula being defined in the Specification):

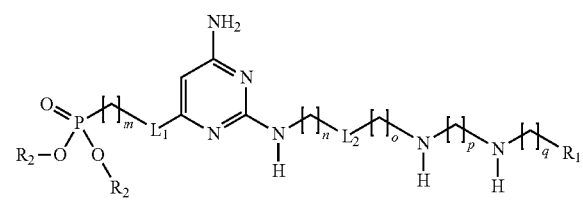

The method can be used to treat cancer and myocardial infarction.

10 Claims, No Drawings

SUBSTITUTED PYRIMIDINES FOR MOBILIZING CELLS EXPRESSING A TYPE 4 CXC CHEMOKINE RECEPTOR

BACKGROUND

Chemokines are a family of cytokines that regulate the adhesion and transendothelial migration of leukocytes during an immune or inflammatory reaction (Mackay C. R., Nat. Immunol., 2001, 2:95; Olson et al., Am. J. Physiol. Regul. Integr. Comp. Physiol., 2002, 283:R7). They also regulate trafficking and homing of T cells and 13 cells, contributing to the development of lymphopoietic and hematopoietic systems (Ajuebor et al., Biochem. Pharmacol., 2002, 63:1191).

Approximately 50 chemokines have been identified in humans. They can be classified into 4 subfamilies, i.e., CXC, CX3C, CC, and C chemokines, based on the positions of the conserved cysteine residues at the N-terminal (Onuffer et al., Trends Pharmacol Sci., 2002, 23:459). Stromal-derived factor-1 (SDF-1), a CXC chemokine, plays key roles in trafficking and retention of malignant stem cells in the bone marrow microenvironment (Nervi et al., Blood, 2009, 24:6206-6214), as well as in homing and mobilization of hematopoietic stem cells and endothelial progenitor cells (Bleul et al., J. Exp. Med., 1996, 184:1101; and Gazzit et al., Stem Cells, 2004, 22:65-73). The physiological function of SDF-1 is mediated by the type 4 CXC chemokine Receptor (CXCR4).

The protective tumor microenvironment is increasingly being recognized as a critical factor in resistance of chemotherapeutic agents. A chemotherapeutic agent is a drug that inhibits cancer cell growth. There is a need to develop agents that mobilize tumor cells from their protective microenvironment to the peripheral blood and make them more accessible to chemotherapeutic agents.

Heart failure in patients who have survived myocardial infarction (MI) remains a major health problem. It is known that mobilizing hematopoietic stem cells, mesenchymal stem cells, and endothelial progenitor cells promotes cardiac functional recovery after MI. Thus, there is also a need to develop agents to mobilize such cells, thereby improving the heart function of post-MI patients.

SUMMARY

This invention is based on the discovery that certain 4-amino-pyrimidine compounds are effective in mobilizing cells expressing CXCR4 into the peripheral circulation.

In one aspect, this invention features mobilizing cells expressing CXCR4, i.e., cancer cells, endothelial progenitor cells, mesenchymal stem cells, and hematopoietic stem cells, into the peripheral circulation by contacting the cells with an effective amount of a 4-amino pyrimidine compound of formula (I) shown below:

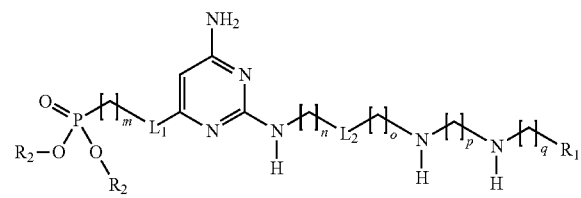

In this formula, $R_1$ is $C_{3-20}$ cycloalkyl, each $R_2$ is H or $C_{1-6}$ alkyl, $L_1$ is $C_{3-20}$ heterocycloalkyl, $L_2$ is $C_{3-20}$ cycloalkyl, and m, n, o, p, and q are each independently 0-6.

Referring to formula (I), a subset of the 4-amino-pyrimidine compounds described above are those in which $L_1$ is

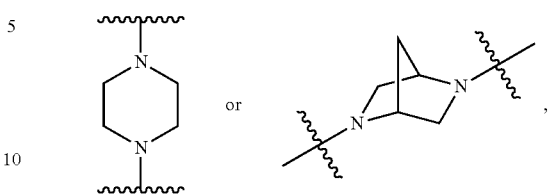

$L_2$ is cyclohexylene, $R_1$ is cyclohexlene or

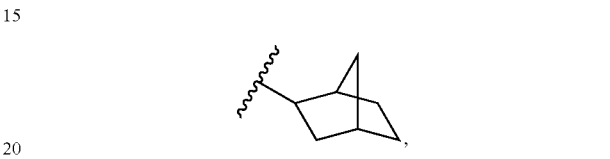

$R_2$ is H, and m, n, o, p, and q are each independently 0-3.

The term "alkyl" refers to a saturated, linear or branched hydrocarbon moiety, such as —$CH_3$ or branched —$C_3H_7$. The term "cycloalkyl" refers to a saturated, non-aromatic, monocyclic, bicyclic, tricyclic, or tetracyclic hydrocarbon moiety, such as cyclohexyl, cyclohexen-3-yl, or adamantyl. The term "heterocycloalkyl" refers to a saturated, non-aromatic, monocyclic, bicyclic, tricyclic, or tetracyclic moiety having one or more ring heteroatoms (e.g., N, O, or S), such as 4-tetrahydropyranyl or 4-pyranyl.

Alkyl, cycloalkyl, and heterocycloalkyl mentioned herein include both substituted and unsubstituted moieties, unless specified otherwise. Possible substituents on alkyl, cycloalkyl, and heterocycloalkyl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyl, and halogen.

The 4-amino-pyrimidine compounds described above include the compounds themselves, as well as their salts, prodrugs, and solvates, if applicable. A salt, for example, can be formed between an anion and a positively charged group (e.g., amino) on a 4-amino-pyrimidine compounds. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a 4-amino-pyrimidine compound. Suitable cations include sodium ion, potassium ion, magnesium ion, calcium ion, and an ammonium cation such as tetramethylammonium ion. The 4-amino-pyrimidine compounds also include those salts containing quaternary nitrogen atoms. Examples of prodrugs include esters and other pharmaceutically acceptable derivatives, which, upon administering to a subject, are capable of providing active 4-aminopyrimidine compounds. A solvate refers to a complex formed between an active 4-amino-pyrimidine compound and a pharmaceutically acceptable solvent. Examples of a pharmaceutically acceptable solvent include water, ethanol, isopropanol, ethyl acetate, acetic acid, and ethanolamine.

In two other aspects, this invention features a method of treating a cancer patient by mobilizing cancer cells to a chemotherapeutic agent and a method of treating a myocardial infarction patient using one or more of the 4-amino-pyrimidine compounds described above. Each method includes administering to a patient in need thereof an effective amount of this compound.

The term "treating" or "treatment" refers to administering one or more 4-amino-pyrimidine compound to a patient in need thereof, with the purpose to confer a therapeutic effect, e.g., to cure, relieve, alter, affect, or ameliorate the disease. "An effective amount" refers to the amount of an active compound that is required to confer the therapeutic effect. Effective doses will vary, as recognized by those skilled in the art, depending on the types of diseases treated, route of administration, excipient usage, and the possibility of co-usage with other therapeutic treatment.

Cancer is a class of diseases in which a group of cells having the capacity for autonomous growth, i.e., an abnormal state or condition characterized by rapidly proliferating cell growth and sometimes tumor metastasis. Examples of cancers include, but are not limited to, breast cancer cell, lung cancer, a prostate cancer, acute myelogenous leukemia, and acute lymphoblastic leukemia.

A subject in need of the above-described treatment can also be concurrently administered with an effective amount of one or more of the 4-amino-pyrimidine compounds described above and an effective amount of one or more other therapeutic agents. The therapeutic agents include a chemotherapeutic agent. For example, one can use a combination of such a 4-amino-pyrimidine compound and a chemotherapeutic agent to treat cancers. The term "concurrently administered" refers to administering two or more active agents at the same time or at different times during the period of treatment. An example of concurrent administration is to apply a solid or liquid mixture of the two or more active agents to a patient. Without being bound by theory, in treating cancer (e.g., acute myeloid leukemia and acute lymphoblastic leukemia), the 4-amino-pyrimidine compound acts as a "chemosensitizer" to mobilize cancer cells from bone marrow and the chemotherapeutic agent then kills these cancer cells, thereby resulting in enhanced treatment effect.

Myocardial infarction, commonly known as heart attack, is a medical emergency that occurs when a portion of the heart is deprived of oxygen because of blockage of one of the coronary arteries, which supply the heart muscle (myocardium) with blood.

Without being bound by theory, in treating myocardial infarction, the 4-amino-pyrimidine compound mobilizes endothelial progenitor cells, mesenchymal stem cells, and hematopoietic stem cells into the peripheral circulation, reducing inflammatory cytokine production and resulting in anti-inflammation or immunomodulation.

To practice the method of the present invention, a composition having one or more the 4-amino-pyrimidine compounds described above can be administered parenterally or orally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique. The composition can take the form of solutions, suspensions, emulsion, tablets, pills, capsules, powders, microparticles, or nanoparticles. It can be also formulated to achieve controlled release or sustained release of the active ingredients.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

The details of one or more embodiments are set forth in the description below. Other features, objects, and advantages of the embodiments will be apparent from the description and the claims.

DETAILED DESCRIPTION

The method described herein uses 4-amino-pyrimidine compounds to mobilize cells expressing CXCR4 into the peripheral circulation for treatment of cancer or myocardial infarction. Shown below are exemplary compounds 1-5:

Compound 1

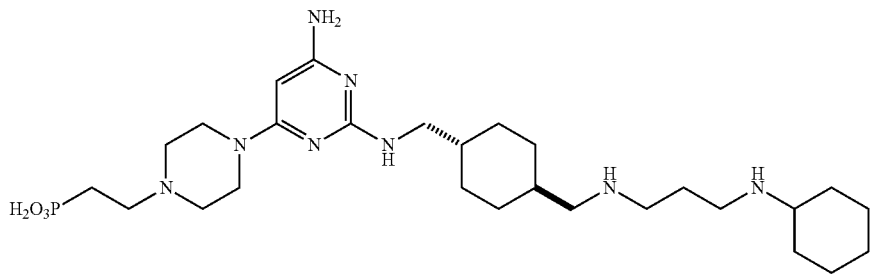

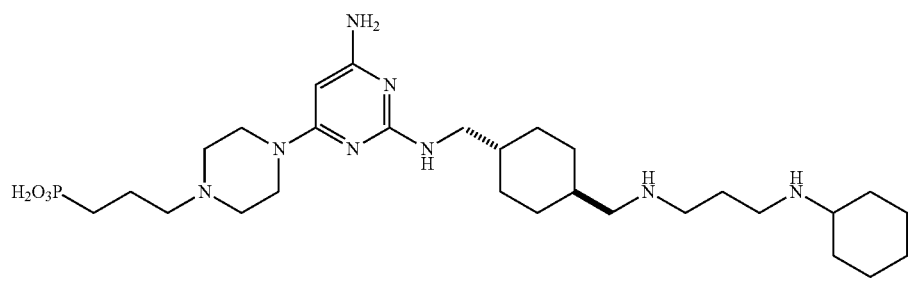

Compound 2

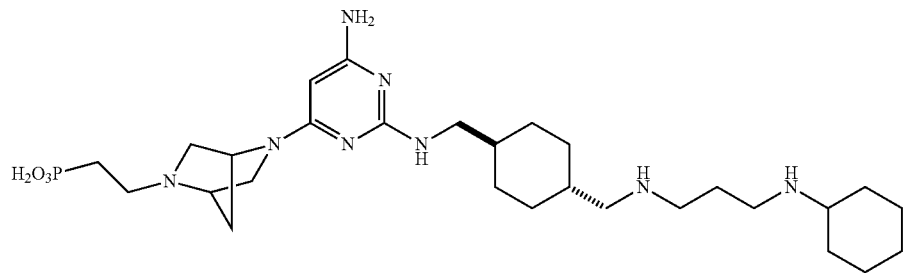

Compound 3

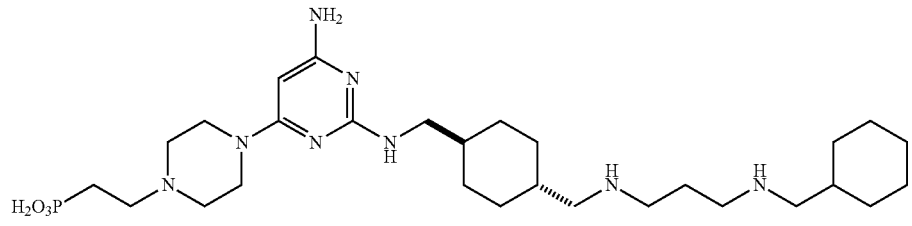

Compound 4

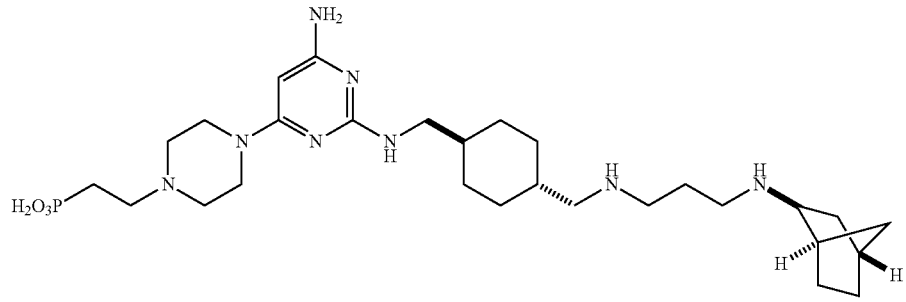

Compound 5

The 4-amino-pyrimidine compounds described above can be prepared by methods well known in the art.

Scheme I below depicts a route for synthesizing certain compounds of Formula (I). Compound A containing two halo groups reacts with the amino compound B to give compound C, which then reacts with aldehyde D to produce compound E. An amino group in compound E is protected with a Boc group. Compound F thus obtained reacts with compound G to afford compound H. Alkylation of compound H followed by deprotection and hydrolysis affords compound J via compound I.

Scheme I

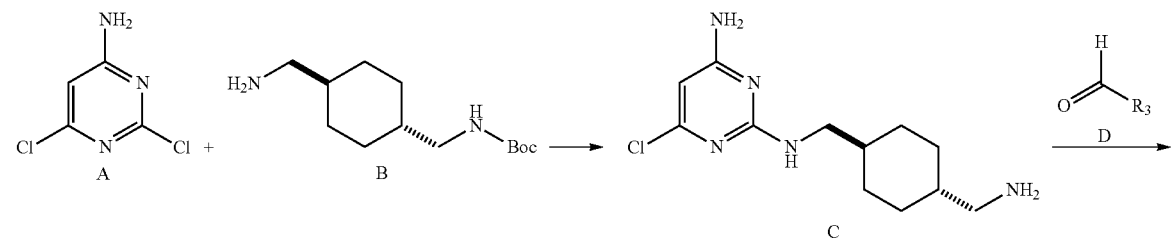

-continued

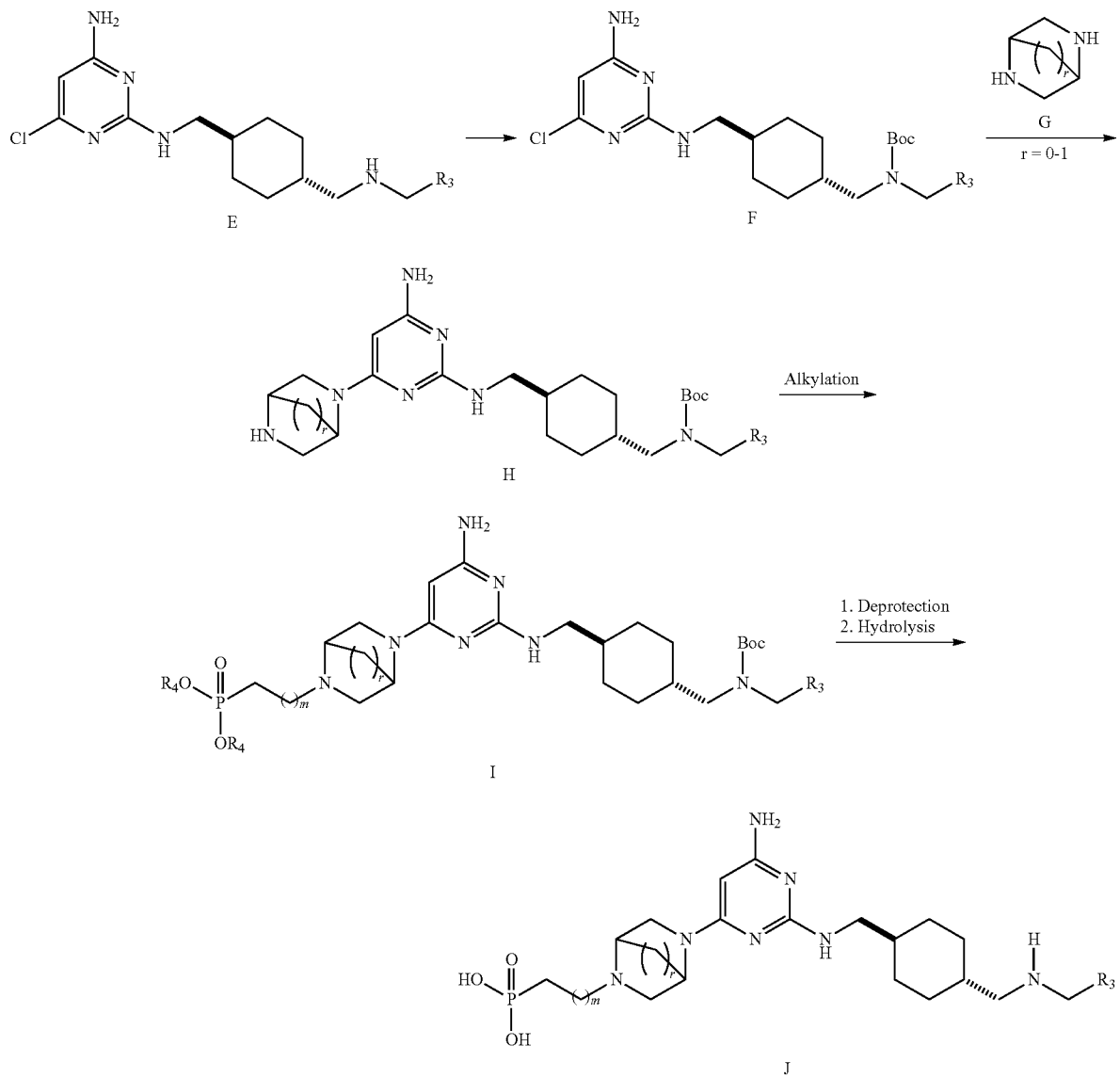

A compound thus synthesized can be purified by methods such as column chromatography, high-pressure liquid chromatography, and recrystallization.

The intermediates used in the scheme described above are either commercially available or can be prepared by methods known in the art. The scheme can also include more steps, either before or after the steps described specifically therein, to add or remove suitable protecting groups to synthesize other compounds of formula (I). In addition, various synthetic steps can be performed in an alternate order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 2$^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1
Preparation of Compound 1
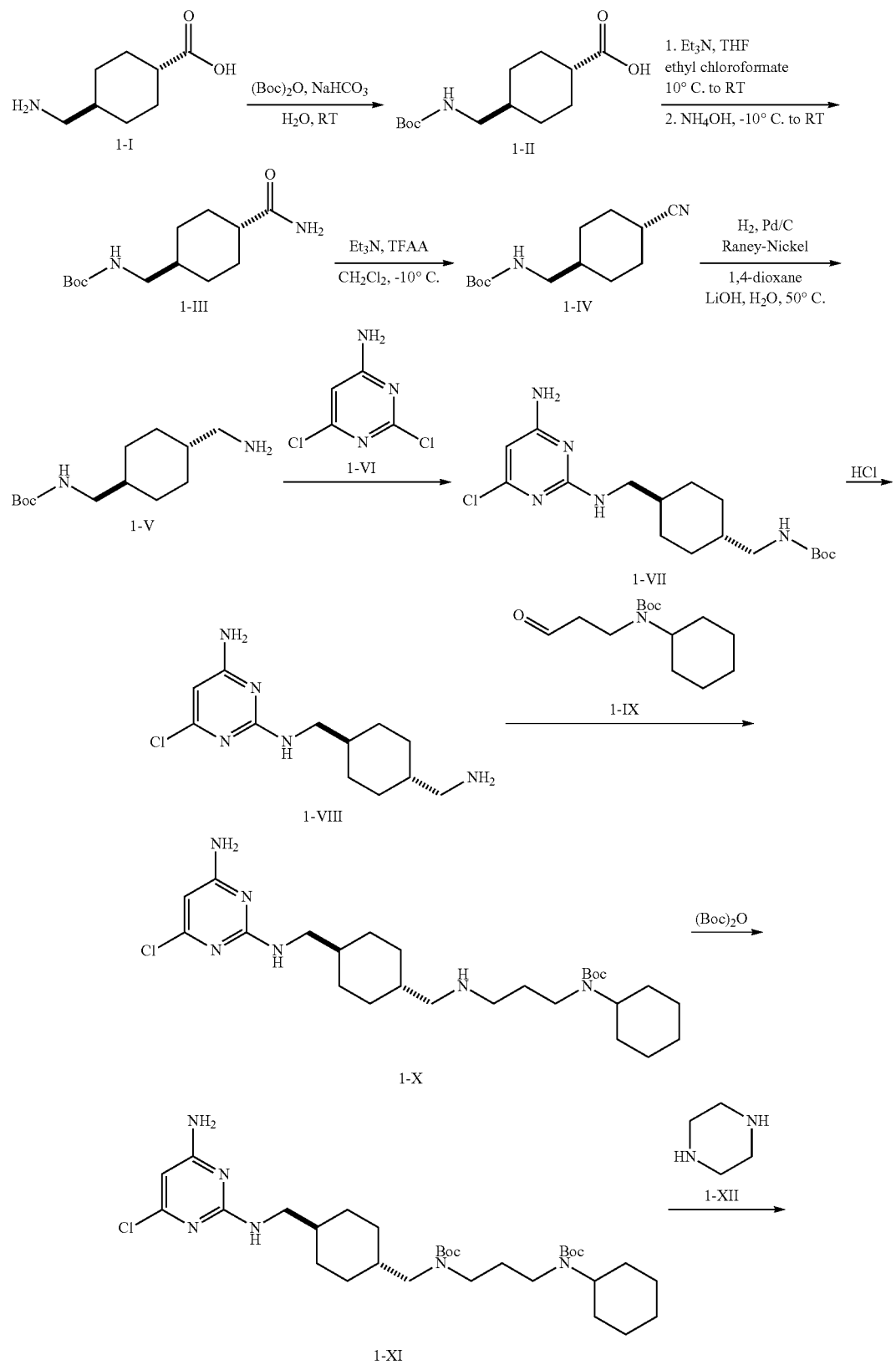

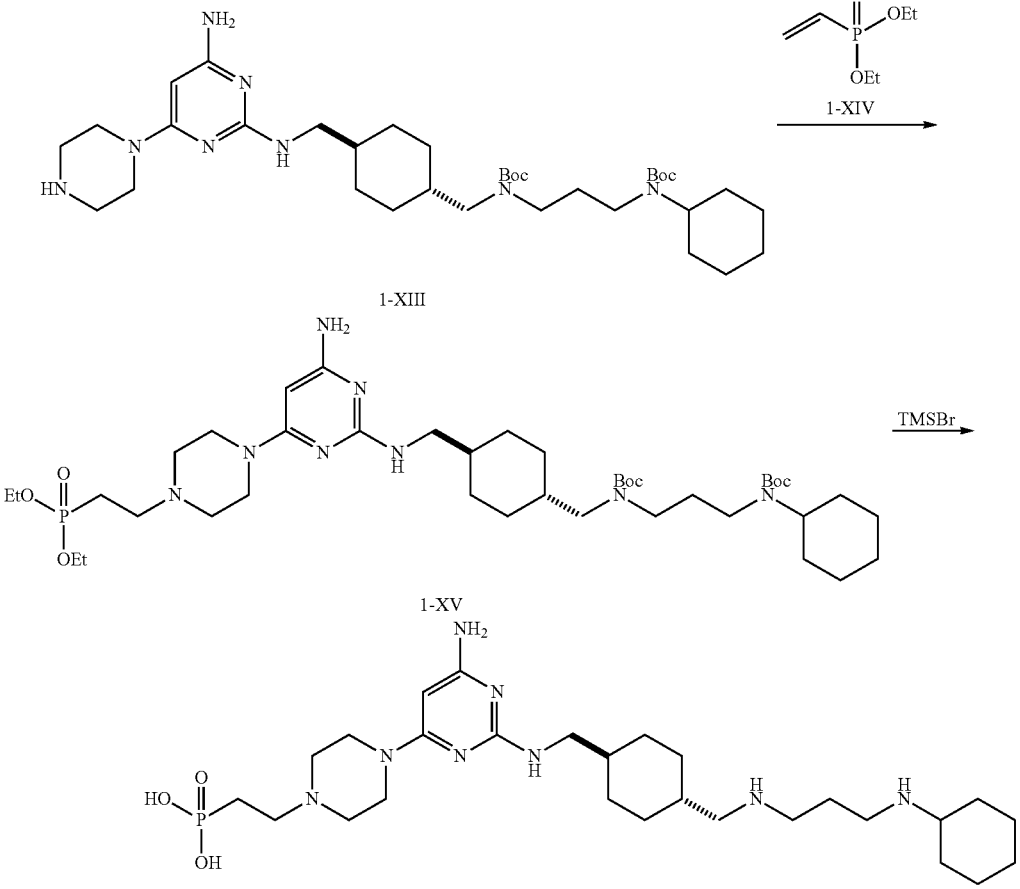

Compound 1

Water (10.0 L) and (Boc)$_2$O (3.33 kg, 15.3 mol) were added to a solution of trans-4-aminomethyl-cyclohexanecarboxylic acid (compound 1-I, 2.0 kg, 12.7 mol) and sodium bicarbonate (2.67 kg, 31.8 mol). The reaction mixture was stirred at ambient temperature for 18 hours. The aqueous layer was acidified with concentrated hydrochloric acid (2.95 L, pH=2) and then filtered. The resultant solid was collected, washed three times with water (15 L), and dried in a hot box (60° C.) to give trans-4-(tert-butoxycarbonylamino-methyl)-cyclohexanecarboxylic acid (compound 1-II, 3.17 kg, 97%) as a white solid. R$_f$=0.58 (EtOAc). LC-MS m/e 280 (M+Na$^+$). $^1$H NMR (300 MHz, CDCl$_3$) δ 4.58 (brs, 1H), 2.98 (t, J=6.3 Hz, 2H), 2.25 (td, J=12, 3.3 Hz, 1H), 2.04 (d, J=11.1 Hz, 2H), 1.83 (d, J=11.1 Hz, 2H), 1.44 (s, 9H), 1.35~1.50 (m, 3H), 0.89~1.03 (m, 2H). $^{13}$C NMR (75 MHz, CDCl$_3$) δ 181.31, 156.08, 79.12, 46.41, 42.99, 37.57, 29.47, 28.29, 27.96. M.p. 134.8~135.0° C.

A suspension of compound 1-II (1.0 kg, 3.89 mol) in THF (5 L) was cooled at −10° C. and triethyl amine (1.076 L, 7.78 mol) and ethyl chloroformate (0.441 L, 4.47 mol) were added below −10° C. The reaction mixture was stirred at ambient temperature for 3 hours. The reaction mixture was then cooled at −0.10° C. again and NH$_4$OH (3.6 L, 23.34 mol) was added below −10° C. The reaction mixture was stirred at ambient temperature for 18 hours and filtered. The solid was collected and washed three times with water (10 L) and dried in a hot box (60° C.) to give trans-4-(tert-butoxycarbonyl-amino-methyl)-cyclohexanecarboxylic acid amide (compound 1-III, 0.8 kg, 80%) as a white solid. Rf=0.23 (EtOAc). LC-MS m/e 279, M+Na$^+$. $^1$H NMR (300 MHz, CD$_3$OD) δ 6.63 (brs, 1H), 2.89 (t, J=6.3 Hz, 2H), 2.16 (td, J=12.2, 3.3 Hz, 1H), 1.80~1.89 (m, 4H), 1.43 (s, 9H), 1.37~1.51 (m, 3H), 0.90~1.05 (m, 2H). $^{13}$C NMR (75 MHz, CD$_3$OD) δ 182.26, 158.85, 79.97, 47.65, 46.02, 39.28, 31.11, 30.41, 28.93. M.p. 221.6~222.0° C.

A suspension of compound 1-III (1.2 kg, 4.68 mol) in CH$_2$Cl$_2$ (8 L) was cooled at −10° C. and triethyl amine (1.3 L, 9.36 mol) and trifluoroacetic anhydride (0.717 L, 5.16 mol) were added below −10° C. The reaction mixture was stirred for 3 hours. After water (2.0 L) was added, the organic layer was separated and washed with water (3.0 L) twice. The organic layer was then passed through silica gel and concentrated. The resultant oil was crystallized by methylene chloride. The crystals were washed with hexane to give trans-(4-cyano-cyclohexylmethyl)-carbamic acid tert-butyl ester (compound 1-IV, 0.95 kg, 85%) as a white crystal. R$_f$=0.78 (EtOAc). LC-MS m/e 261, M+Na$^+$. $^1$H NMR (300 MHz, CDCl$_3$) δ 4.58 (brs, 1H), 2.96 (t, J=6.3 Hz, 2H), 2.36 (td, J=12, 3.3 Hz, 1H), 2.12 (dd, J=13.3, 3.3 Hz, 2H), 1.83 (dd, J=13.8, 2.7 Hz, 2H), 1.42 (s, 9H), 1.47~1.63 (m, 3H), 0.88~1.02 (m, 2H). $^{13}$C NMR (75 MHz, CDCl$_3$) δ 155.96, 122.41, 79.09, 45.89, 36.92, 29.06, 28.80, 28.25, 28.00. M.p. 100.4~100.6° C.

Compound 1-IV (1.0 kg, 4.196 mol) was dissolved in a mixture of 1,4-dioxane (8.0 L) and water (2.0 L). To the reaction mixture were added lithium hydroxide monohydrate (0.314 kg, 4.191), Raney-nickel (0.4 kg, 2.334 mol), and 10% palladium on carbon (0.46 kg, 0.216 mol) as a 50% suspension in water. The reaction mixture was stirred under hydrogen atmosphere at 50° C. for 20 hours. After the catalysts were removed by filtration and the solvents were removed in vacuum, a mixture of water (1.0 L) and CH$_2$Cl$_2$ (0.3 L) was added. After phase separation, the organic phase was washed with water (1.0 L) and concentrated to give trans-(4-aminomethyl-cyclohexylmethyl)-carbamic acid tert-butyl ester (compound 1-V, 0.97 kg, 95%) as pale yellow thick oil. R$_f$=0.20 (MeOH/EtOAc=9/1). LC-MS m/e 243, M+H$^+$. $^1$H NMR (300 MHz, CDCl$_3$) δ 4.67 (brs, 1H), 2.93 (t, J=6.3 Hz, 2H), 2.48 (d, J=6.3 Hz, 2H), 1.73~1.78 (m, 4H), 1.40 (s, 9H), 1.35 (brs, 3H), 1.19~1.21 (m, 1H), 0.77~0.97 (m, 4H). $^{13}$C NMR (75 MHz, CDCl$_3$) δ 155.85, 78.33, 48.27, 46.38, 40.80, 38.19, 29.87, 29.76, 28.07.

A solution of compound 1-V (806 g) and Et$_3$N (1010 g, 3 eq) in 1-pentanol (2.7 L) was treated with compound 1-VI, 540 g, 1 eq) at 90° C. for 15 hours. TLC showed that the reaction was completed.

Ethyl acetate (1.5 L) was added to the reaction mixture at 25° C. The solution was stirred for 1 hour. The Et$_3$NHCl salt was filtered. The filtrate was then concentrated to 1.5 L (⅙ of original volume) by vacuum at 50° C. Then, diethyl ether (2.5 L) was added to the concentrated solution to afford the desired product 1-VII (841 g, 68% yield) after filtration at 25° C.

A solution of intermediate 1-VII (841 g) was treated with 4N HCl/dioxane (2.7 L) in MeOH (8.1 L) and stirred at 25° C. for 15 hours. TLC showed that the reaction was completed. The mixture was concentrated to 1.5 L (⅕ of original volume) by vacuum at 50° C. Then, diethyl ether (5 L) was added to the solution slowly, and HCl salt of 1-VIII (774 g) was formed, filtered, and dried under vacuum (<10 torr). For neutralization, K$_2$CO$_3$ (2.5 kg, 8 eq) was added to the solution of HCl salt of 1-VIII in MeOH (17 L) at 25° C. The mixture was stirred at the same temperature for 3 hours (pH>12) and filtered (estimated amount of 1-VIII in the filtrate is 504 g).

Aldehyde 1-IX (581 g, 1.0 eq based on mole of 1-VII) was added to the filtrate of 1-VIII at 0-10° C. The reaction was stirred at 0-10° C. for 3 hours. TLC showed that the reaction was completed. Then, NaBH$_4$ (81 g, 1.0 eq based on mole of 1-VII) was added at less than 10° C. and the solution was stirred at 10-15° C. for 1 h. The solution was concentrated to get a residue, which then treated with CH$_2$Cl$_2$ (15 L). The mixture was washed with saturated aq. NH$_4$Cl solution (300 mL) diluted with H$_2$O (1.2 L). The CH$_2$Cl$_2$ layer was concentrated and the residue was purified by chromatography on silica gel (short column, EtOAc as mobile phase for removing other components; MeOH/28% NH$_4$OH=97/3 as mobile phase for collecting 1-X) afforded crude 1-X (841 g).

Then Et$_3$N (167 g, 1 eq) and Boc$_2$O (360 g, 1 eq) were added to the solution of 1-X (841 g) in CH$_2$Cl$_2$ (8.4 L) at 25° C. The mixture was stirred at 25° C. for 15 hours. After the reaction was completed as evidenced by TLC, the solution was concentrated and EtOAc (5 L) was added to the resultant residue. The solution was concentrated to 3 L (½ of the original volume) under low pressure at 50° C. Then, n-hexane (3 L) was added to the concentrated solution. The solid product formed at 50° C. by seeding to afford the desired crude product 1-XI (600 g, 60% yield) after filtration and evaporation.

To compound 1-XI (120.0 g) and piperazine (1-XII, 50.0 g, 3 eq) in 1-pentanol (360 mL) was added Et$_3$N (60.0 g, 3.0 eq) at 25° C. The mixture was stirred at 120° C. for 8 hours. Ethyl acetate (480 mL) was added to the reaction mixture at 25° C. The solution was stirred for 1 h. The Et$_3$NHCl salt was filtered and the solution was concentrated and purified by silica gel (EtOAc/MeOH=2:8) to afforded 1-XIII (96 g) in a 74% yield.

To a solution of 1-XIII (120 g) in MeOH (2.4 L) were added diethyl vinyl phosphonate (1-XIV, 45 g, 1.5 eq) at 25° C. The mixture was stirred under 65° C. for 24 hours. TLC and HPLC showed that the reaction was completed. The solution was concentrated and purified by silica gel (MeOH/CH$_2$Cl$_2$=8/92) to get 87 g of 1-XV (53% yield, purity>98%, each single impurity<1%) after analyzing the purity of the product by HPLC.

To a solution of 2-II (300 g) in CH$_2$Cl$_2$ (1800 mL) was added TMSBr (450 g, 8 eq) at 10-15° C. for 1 hour. The mixture was stirred at 25° C. for 15 hours. The solution was concentrated to remove TMSBr and solvent under vacuum at 40° C. CH$_2$Cl$_2$ was added to the mixture to dissolve the residue. TMSBr and solvent were removed under vacuum again to obtain 360 g crude solid after drying under vacuum (<1 torr) for 3 hours. Then, the crude solid was washed with 7.5 L IPA/MeOH (9/1) to afford compound 3 (280 g) after filtration and drying at 25° C. under vacuum (<1 torr) for 3 hours. Crystallization by EtOH gave hydrobromide salt of compound 3 (190 g).

CI-MS (M$^+$+1): 567.0.

Example 2

Preparation of Compound 2

Compound 2 was prepared in the same manner as described in Example 1 except that diethyl-1-bromopropylphosphonate was used instead of diethyl vinyl phosphonate.

CI-MS (M$^+$+1): 582.0

Example 3

Preparation of Compound 3

Compound 3 was prepared in the same manner as described in Example 1 except that 2,5-diaza-bicyclo[2.2.1]heptane was used instead of piperazine.

CI-MS (M$^+$+1): 579.4

Example 4
Preparation of Compound 4
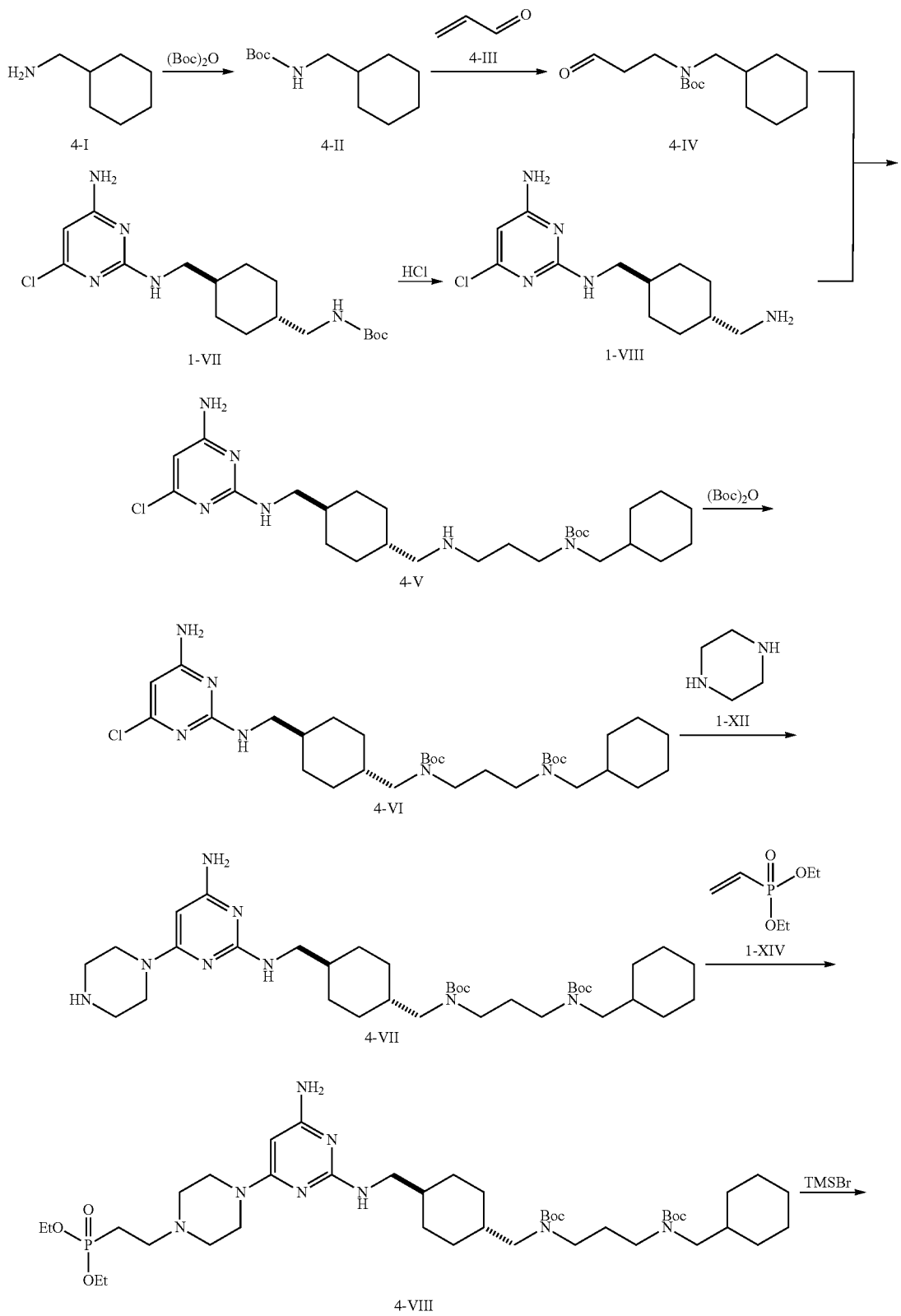

-continued

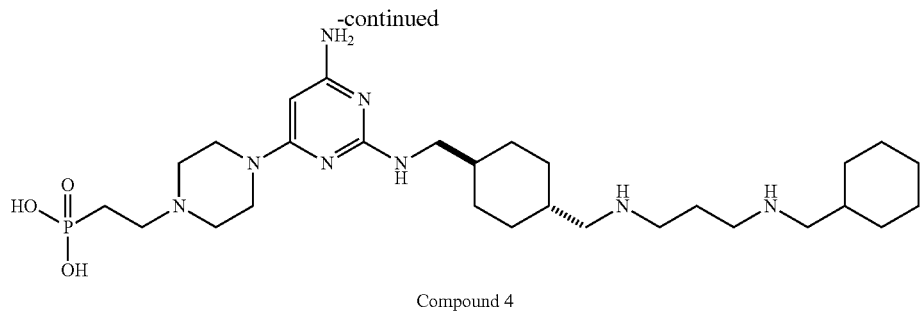

Compound 4

Intermediate 1-VII was prepared as described in Example 1.

A solution of compound cyclohexylmethanamine (4-I, 3.0 g) and Boc$_2$O (5.8 g) in CH$_2$Cl$_2$ (30 mL) was added to Et$_3$N (5.0 mL) at 25° C. for 15 hours. The solution was then concentrated and the resultant residue was purified by column chromatography on silica gel (using EtOAc and Hexane as an eluant) to give intermediate 4-II (6.5 g) in a 49% yield.

To intermediate 4-II (3.0 g) and DL-10-camphorsulfonic acid (450 mg) in CH$_2$Cl$_2$ (15 ml) was added acrolein (4-III, 2.72 g) at 0° C. The reaction was stirred at 25° C. for 15 hours. The solution was concentrated and purified by chromatography on silica gel (EtOAc/Hex=4:1) to give intermediate 4-IV (2.4 g) in a 63% yield.

A solution of intermediate 1-VII (2.2 g) was treated with 4N HCl/dioxane (10 mL) in MeOH (20 mL) and stirred at 25° C. for 15 hours. TLC showed that the reaction was completed. The mixture was concentrated and HCl salt of 1-VIII was formed, filtered, and dried under vacuum (<10 torr). For neutralization, K$_2$CO$_3$ (1.5 g) was added to the solution of HCl salt of 1-VIII in MeOH (20 mL) at 25° C. The mixture was stirred at the same temperature for 3 hours (pH>12) and filtered.

Aldehyde 4-IV (1.8 g) was added to the filtrate at 0-10° C. The mixture was stirred at 0-10° C. for 3 hours. TLC showed that the reaction was completed. Then, NaBH$_4$ (225 mg) was added at less than 10° C. and the solution was stirred at 10-15° C. for 1 h. The solution was concentrated to provide a residue, which was then treated with CH$_2$Cl$_2$ (30 mL). The mixture was washed with saturated aq. NH$_4$Cl solution. The CH$_2$Cl$_2$ layer was concentrated and the residue was purified by chromatography on silica gel (short column, EtOAc as mobile phase for removing other components; MeOH/28% NH$_4$OH=97/3 as mobile phase for collecting 4-V) to afford crude 4-V. The crude product was used in the next step without purification.

Et$_3$N (820 mg) and Boc$_2$O (470 mg) were added to the solution of crude 4-V in CH$_2$Cl$_2$ (10 mL) at 25° C. The mixture was stirred at 25° C. for 15 hours. TLC showed that the reaction was completed. The solution was concentrated and purified by chromatography on silica gel (EtOAc/Hex=1: 1) to give intermediate 4-VI (1.3 g) in a 35% yield.

To compound 4-VI (1.3 g) and piperazine (1-XII, 1.08 g) in 1-pentanol (26 mL) was added Et$_3$N (1.26 g) at 25° C. The mixture was stirred at 120° C. for 8 hours. TLC showed that the reaction was completed. The solution was concentrated and purified by chromatography on silica gel (EtOAc/ MeOH=3:7) to give intermediate 4-VII (1.0 g) in a 76% yield.

To a solution of 4-VII (1 g) in MeOH (20 mL) was added diethyl vinyl phosphonate (1-XIV, 366 mg, 1.5 eq) at 25° C. The mixture was stirred under 65° C. for 24 hours. TLC and HPLC showed that the reaction was completed. The solution was concentrated and purified by silica gel (MeOH/ CH$_2$Cl$_2$=8/92) to get 400 mg of 4-VIII in a 32% yield.

To a solution of 4-VIII (300 mg) in CH$_2$Cl$_2$ (2 mL) was added TMSBr (439 mg, 8 eq.) at 10-15° C. for 1 hour. The mixture was stirred at 25° C. for 15 hours. The solution was concentrated to remove TMSBr and the solvent under vacuum at 40° C. CH$_2$Cl$_2$ was added to the mixture to dissolve the residue. TMSBr and the solvent were removed under vacuum again to obtain a crude solid, which was washed with IPA/MeOH (9/1) to afford compound 4 after filtration and drying at 25° C. under vacuum (<1 torr) for 3 hours. Crystallization in EtOH gave hydrobromide salt of compound 4 (100 mg).

CI-MS (M$^+$+1): 581.4

Example 5

Preparation of Compound 5

Compound 5 was prepared in the same manner as described in Example 4 except that exo-2-aminonorbornane was used instead of cyclohexylmethanamine.

CI-MS (M$^+$+1): 579.4

Example 6

Efficacy in Treating Leukemia Engrafted Mice

In vivo efficacy of the 4-amino-pyrimidine compounds in treating cancer was assessed using leukemia engrafted mice (transplanted with leukemia cells).

Mononuclear human leukemia cells were prepared using Ficoll gradient centrifugation and cryopreserved in liquid nitrogen. The frozen cells were thawed quickly and washed with PBS to remove the cryopreservation reagent. NOD/ SCID mice (Institute of Cellular and Organismic Biology, Academia Sinica) were preconditioned with 200 centigray of total body irradiation at 6-8 weeks of age. The leukemia cells were then transplanted to the preconditioned NOD/SCID mice via tail vein. The resulting leukemia blast cells, i.e., T acute lymphoblastic leukemia (T-ALL) cells and acute myelogenous leukemia (AML) cells, were recovered from spleen and used in experiments as described below.

Mice were monitored for leukemia cell engraftment and dissemination by the appearance of human CD45$^+$ cells in mouse peripheral blood, which were sampled weekly after the 3$^{rd}$ week of cell transplantation. Peripheral blood samples were taken from the tail vein and red blood cells were lysed in ammonium chloride and resuspended in Phosphate buffered saline (PBS) plus 2% Fetal Bovine Serum (FBS) before cell staining. Circulating mononuclear cells were immunestained with Fluorescein Isothiocyanate-conjugated antimouse CD45 antibodies (Pharmingen) and Phycoerythrin-conjugated anti-human CD45 antibodies (Pharmingen) with one spare aliquot for isotype staining control. After immunostaining, cells were washed, suspended in PBS plus 2% FBS, and analyzed using FACS Calibur (BD Biosciences). These cells were also stained with propidium iodide (PI) as a marker of cell viability. Non-viable cells were gated based on PI uptake; matched isotype controls were run for each sample and used to define gate settings, which excluded at least 99% of the cells in the isotype control. The rate of engraftment and dissemination was previously established as the number of days following transplantation for leukemia cells to disseminate and reach at least a proportion of 1% human CD45$^+$ cells in the peripheral blood.

Enhancement of Efficacy of Ara-C (an Anti-Cancer Chemotherapy Drug) in Treating AML Preconditioned NOD/SCID mice were injected intravenously with AML cells. At day 15, the mice were treated with saline, Ara-c (100 mg/kg), or compound 1 (30 mg/kg)-plus-Ara-c (100 mg/kg). At day 16, the mice received the second dose treatment. Saline and compound 1 were injected intravenously, and Ara-C was injected subcutaneously. In mice co-administered with compound 1 and Ara-C, Ara-C was injected half hour after the injection of compound 1.

The results show that the overall survival time of leukemic mice was significantly prolonged when mice were treated with a combination of compound 1 and Ara-C, as compared with mice treated with Ara-C alone. In addition, the percentage of CD45$^+$ cells at weeks 5 and 6 after the AML injection was reduced significantly among mice receiving the combination of compound 1 and Ara-C treatment compared with mice receiving Ara-C alone. In other words, compound 1 significantly enhanced the efficacy of Ara-c in treating AML.

Enhancement of Efficacy of Vincristine an Anti-Cancer Chemotherapy Drug) in Treating T-all Preconditioned NOD/SCID mice were injected intravenously with T-ALL cells. At day 14, the mice were injected with saline, vincristine (0.5 mg/kg), compound 1 (5 mg/kg)-plus-vincristine (0.5 mg/kg), or compound 1 (20 mg/kg)-plus-vincristine injection. At days 21 and 28, the mice received the second and the third dose treatments, respectively. Saline and compound 1 were injected intravenously, and vincristine was injected intraperitoneally. In mice co-administered with compound 1 and vincristine, vincristine was injected an hour after the injection of compound 1.

The results show that the average survival times of each group are 47±5.6, 73.6±7.1, 85.4±11.8, and 111.8±12.2 days, respectively. Put differently, the overall survival time was significantly prolonged when mice were treated with the combination of compound 1 and vincristine as compared with the group receiving vincristine treatment alone.

Further, CD45$^+$ cells in the peripheral blood were not detected in mice treated with vincristine and compound 1 (5 mg/kg)-plus-vincristine until 8 weeks later, and also not detected in mice treated with compound 1 (20 mg/kg)-plus-vincristine until 10 weeks later. The results indicate that compound 1 and vincristine effectively eliminated CD45$^+$ in the circulation during these time periods.

In sum, compound 1 greatly enhanced the efficacy of vincristine in treating T-ALL.

Mobilizing Human Leukemia Cells (CD45+Cells)

Mice were injected intravenously with compound 1 (30 mg/kg) at day 21 of the leukemia cell implantation. Peripheral blood was collected at baseline, 0.5 h, 1 h, 2 h, 3 h, 6 h, and 24 h. CD45$^+$ cells in the peripheral blood were measured using flow cytometry.

The results show that CD45$^+$ cells circulating in the peripheral blood reached a peak level at 0.5-1 hour after the administering of compound 1, indicating that compound 1 effectively mobilized leukemia cells from bone marrow into the peripheral blood.

Example 7

Efficacy in Treating Myocardial Infarction in Minipigs

Efficacy of 4-amino-pyrimidine compounds in treating myocardial infarction was assessed following the procedures described below.

Minipigs underwent coronary-artery-occlusion for 157±17 min to induce myocardial infarction (MI). Each animal was rejected intravenously with compound 1 (2.85 mg/Kg) or saline at day 3 post-MI. At day 7 post-MI, each animal received the second dose treatment.

All data are expressed as mean±SD. Statistical analysis was performed using Prism 5 software (GraphPad Software, San Diego, Calif.). Group differences were assessed by the Mann Whitney test. A p value<0.05 was considered statistically significant. Repeated measurements were analyzed with a 2-way analysis of variance followed by mean separation with pair-wise Bonferroni corrections.

Therapeutic Effect, of Compound 1 on Cardiac Function and Remodeling

The therapeutic effect of compound 1 was assessed using magnetic resonance imaging (MRI) at day 3 (prior to the treatment) and week 12 post-MI, following the procedures described in Cardiovascular Research, 2009, 81:482-490. The end-diastolic volume (EDV) and end-systolic volume (ESV) were assessed based on the maximal and minimal values of the volume-time curve. These values were normalized according to body surface area and used to compute the LV ejection fraction (EF). The left ventricular (LV) mass was computed as the difference between the LV epicardial volume at the end-diastole and the LVEDV, multiplied by the density of the myocardium (1.05 g/mL).

At week 12 post-MI, EDV and ESV increased in both control and compound 1-treated groups. In the control group, the left ventricular ejection fraction (LVEF) declined from 54±8% at baseline to 46±10% at 12-week post-MI (p=0.0125). By contrast, the compound 1-treated group showed a preserved LVEF (50.7±4.9 at the baseline vs. 50.7±4.3 at 12-week post-MI; p=0.3723). The difference in the changes of LVEF from the baseline between the two groups was statistically significant (p=0.029). Although the LV systolic function was well preserved, treatment of MI pigs with compound 1 did not significantly attenuate the LV hypertrophy, which is considered to contribute to the increase in LV mass from the baseline.

The results indicate that treatment of compound 1 prevented ventricular dysfunction at week 12 post-MI without apparent effect on cardiac structural change.

Effects of Compound 1 on Myocardial Viability, Infarct Size, and Angiogenesis

The myocardial viability effect of compound 1 was evaluated using thallium single-photon emission computed tomography ($^{201}$Tl SPECT) rest-redistribution scintigraphy at day 7 (prior to the second dose treatment) and week 12 post-MI. SPECT images were obtained with a dual-head gamma camera (Millenium, GE Medical Systems, Milwaukee, Wis., USA) as described in Journal Cardiovascular Imaging, 2007, 23:757-765. The regional SPECT was assessed using the 17-segment model (American Heart Association) and the semiquantitative scoring system of defect of severity and extent. Each segment was scored based on the severity of tracer uptake in a 5-point scoring system (0=normal, 1=equivocal, 2=moderate, 3=severe, and 4=apparent absence of tracer uptake). SRS, the sum of the 17 segmental rest scores, was subsequently calculated.

The changes of SRS from the baseline to 12-week post-MI were not significantly different between the control and the compound 1-treated groups. Scar volumes were measured by using manual planimetry when porcine hearts were harvested at the $12^{th}$ week post-MI. The results confirm that there were no differences in infarct size between the control and the compound 1-treated groups (6.4±2.1% vs. 6.8±1.4% of LV mass). Moreover, compound 1 did not significantly increase the vessel density in the peri-infarct myocardium (49.6±19.2/$mm^2$ vs. 43.5±11.2/$mm^2$).

The results further confirm that compound 1 improves cardiac contractile function without an apparent effect on cardiac structural change.

Effects of Compound 1 on Myocardial and Systemic Inflammation

Myocardial inflammation was determined by gene expression of TNF-a, IL-13, and IL-6 in the infarct area at both day 7 and week 12 post-MI. The levels of TNF-a, IL-13, and IL-6 were significantly reduced in the compound 1-treated group at day 7 post-MI compared with the control group. Additionally, compound 1-treated minipigs had significantly lower plasma levels of TNF-a (349±60 vs. 186±41 pg/mL, n=6, p<0.001), IL-13 (436±89 vs. 163±54, n=6, p<0.001), and IL-6 (405±109 vs. 204±54 pg/mL, n=6, p<0.01) at day 7 post-MI than the control group. Further, the levels of TNF-a, IL-13, and IL-6 in compound 1-treated minipigs were significantly lower during week 6-12 period of post-MI than those of the control group.

The result indicate that compound 1 improved cardiac function by significantly decreasing myocardial expression of pro-inflammatory cytokines, i.e., TNF-a, IL-13, and IL-6.

Mobilization Effects of Compound 1 on Hematopoietic Stem Cells

MI minipigs were injected intravenously with saline or compound 1 (2.85 mg/Kg) twice at a 72-hour interval. Peripheral blood (PB) was collected at baseline, 0.5 h, 1 h, 2 h, 3 h, 6 h, and 24 h. Leukocytes were isolated using density gradient centrifugation (Ficoll-Paque, GE Healthcare Bio-Sciences AB), labeled with primary antibodies to CD34 (YST01; R&D), CD133 (AC133; Miltenyi Biotec), and CD271 (ME20.4; Miltenyi Biotec), and analyzed using a FACS Calibur instrument (BD Bioscience) and Cell Quest Software (Becton Dickinson). The frequency of $CD34^+$, $CD133^+$, or $CD271^+$ events in the PB was expressed as the percentage of positive cells among all leukocytes after electronic gating on viable cells. The number of positive cells per microliter of cells was calculated by multiplying the frequency of $CD34^+$, $CD133^+$, or $CD271^+$ events by the total leukocyte count. To evaluate mobilization effects of compound 1, the fold-increase from the baseline was calculated as [(events at post-injection time points)/(events at baseline)]. Similarly, anti-CXCR4 (ab2074; Abcam) was used to confirm the co-expression of CXCR4 on mobilized $CD34^+$, $CD133^+$ cells, and $CD271^+$ cells.

Compared with the control group, compound 1 increased $CD34^+$ and $CD133^+$ cells in the periphery circulation by about 4-fold and 2.65-fold, respectively, at 1-6 hours after the first injection. After the second injection, compound 1 increased peripheral blood $CD34^+$ cells by about 5.1-fold and $CD133^+$ cells about 5.8-fold.

These results indicate that compound 1 was effective in enhancing the circulating stem cell levels in post-MI minipigs.

Mobilization Effects of Compound 1 on Mesenchymal Stem Cells (MSC)

MI minipigs were injected intravenously with saline or compound 1 (2.85 mg/Kg) twice at a 72-hour interval. PB was collected at the baseline, 0.5 h, 1 h, 2 h, 3 h, 6 h, and 24 h. $CD271^+$ cells were isolated immune-magnetically, expanded using IMag™ Anti-Phycoerythrin Magnetic Particles-DM (BD Bioscience), and then incubated with MSC medium consisting of αMEM (Invitrogen) and 10% FBS (Invitrogen) in 75 $mm^2$ flasks to give a cell density of $2 \times 10^5$ $cells/cm^2$. The MSC medium was supplemented with basic fibroblast growth factor and epithelial cell growth factor (10 ng/ml each; R&D Systems). After 24-h incubation, the medium was changed every 3 days. MSC colonies were defined as adherent, clonogenic, nonphagocytic, and fibroblastic in habit (designate as colony-forming units-fibroblastic; CFUFs). Enumeration of MSC-CFUFs was performed after 8 days of incubation using a microscope. Colony-forming efficiency (CFE) was defined as the number of colonies to every $10^6$ cells seeded. Expanded MSC-CFUFs were assessed for both their ability to modulate allogeneic reaction in one-way mixed lymphocyte reaction and phenotypic characteristics.

The data show that compound 1 increased $CD271^+$ cells in the PB about 4-fold and 5.5-fold at 1-3 hours after the first and second dose treatments, respectively. Moreover, the majority of $CD271^+$ cells egressed by Compound 1 expressed CXCR4. Furthermore, CFE was increased about 18-fold (from 0.05±0.02 to 0.92±0.25) and about 6-fold (from 0.55±0.25 to 3.18±0.39) after the first dose and the second dose treatment, respectively (p<0.01). The results indicate that compound 1 mobilized $CXCR4^+$ MSC cells from bone marrow into the periphery circulation.

Mobilization Effect of Compound 1 on Endothelial Progenitor Cells

BALB/c mice (BioLasco) were injected intravenously with saline or compound 1 (60 mg/Kg). Whole blood was collected at 1 h, 2 h, 3 h, 6 h, 18 h, and 24 h. Endothelial progenitor cells ($CD133^+$) were measured using antibody surface staining and flow cytometry (Beckman Coulter, Miami, Fla.).

The data show that compound 1 increased circulating $CD133^+$ endothelial progenitor cells 5.2-10.7 folds within 1-3 hours after a single injection. The results indicate that compound 1 greatly enhanced the mobilization of $CD133^+$ endothelial progenitor cells into the peripheral blood.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for mobilizing cancer cells, endothelial progenitor cells, mesenchymal stem cells and hematopoietic stem cells expressing a CXCR4 chemokine receptor into the peripheral circulation, the method comprising contacting the cells with an effective amount of a compound selected from the group consisting of:

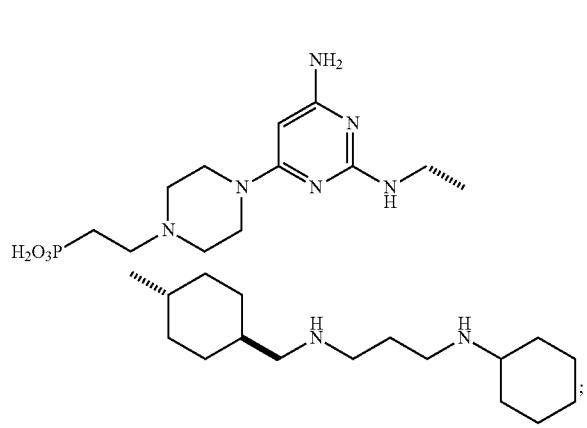

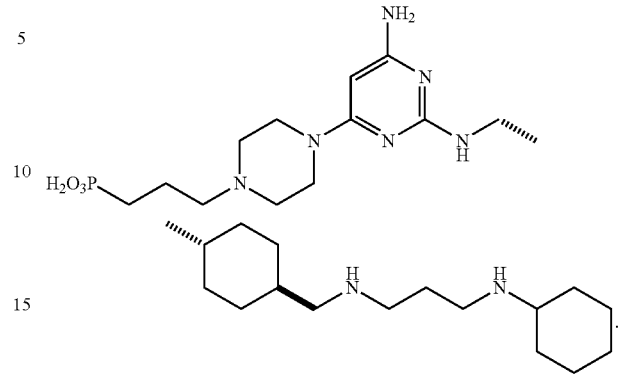

2. The method of claim 1, wherein the compound is:

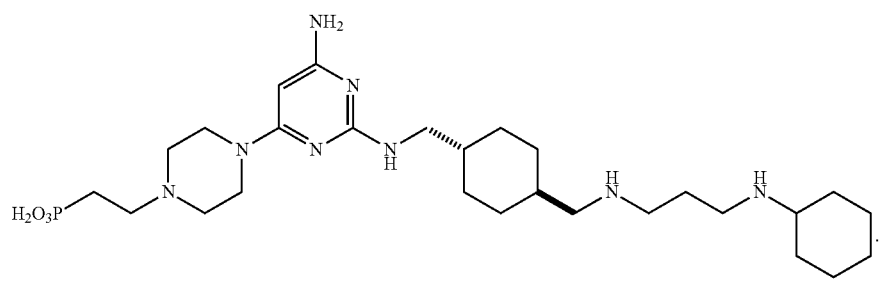

3. A method for sensitizing a cancer cell in a subject to a chemotherapy agent, the method comprising administering to the subject in need thereof an effective amount of a compound selected from the group consisting of:

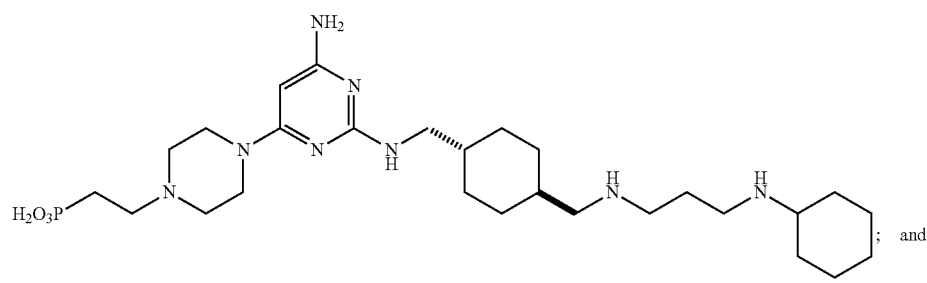

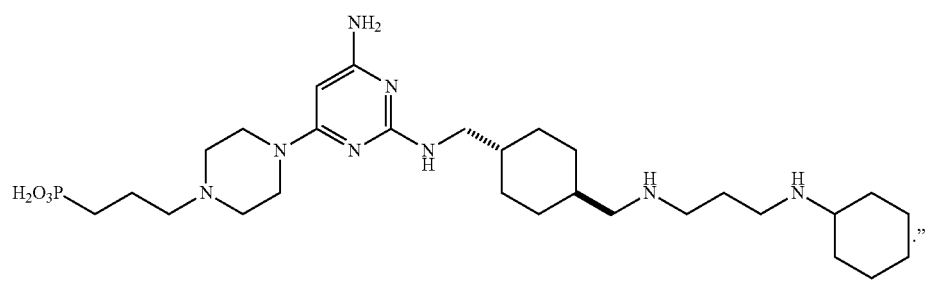

4. The method of claim 3, wherein the cancer cell is selected from the group consisting of a breast cancer cell, a lung cancer cell, and a prostate cancer cell.

5. The method of claim 3, wherein the cancer cell is selected from the group consisting of an acute myelogenous leukemia cell and acute lymphoblastic leukemia cell.

6. The method of claim 3, where the compound is:

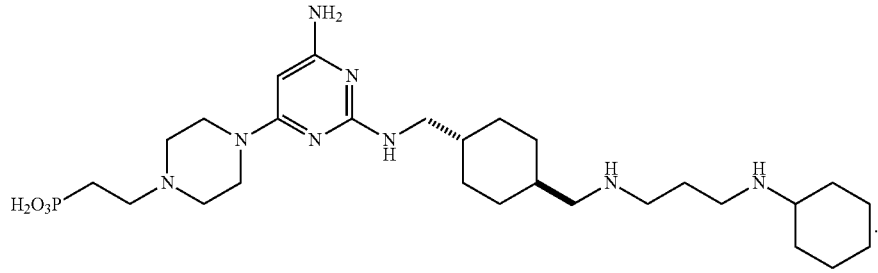

7. The method of claim 4, where the compound is:

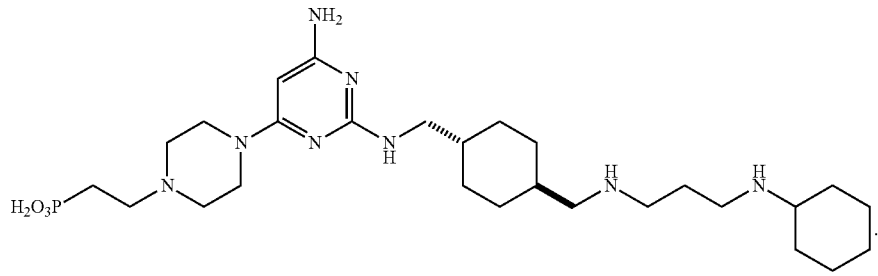

8. The method of claim 5, wherein the compound is:

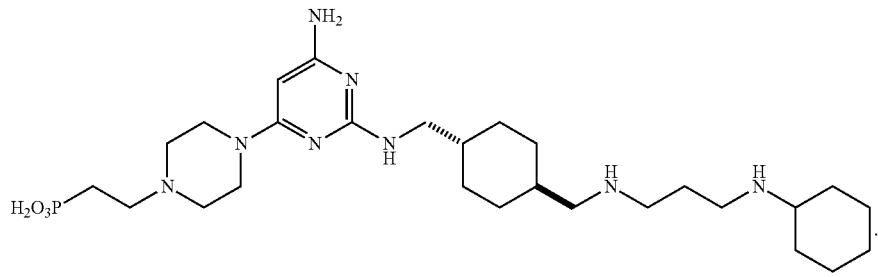

9. A method for treating myocardial infarction in a subject, the method comprising administering to the subject in need thereof an effective amount of a compound selected from the group consisting of:

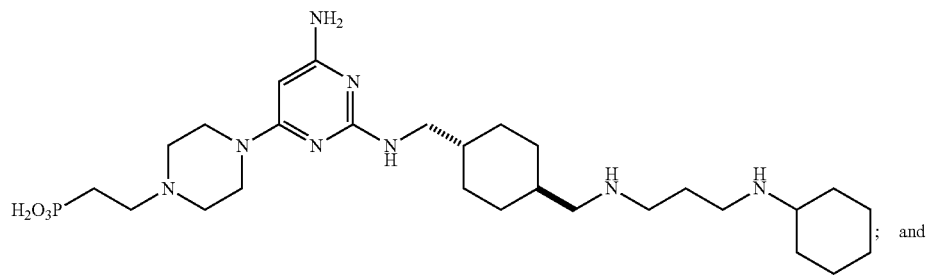

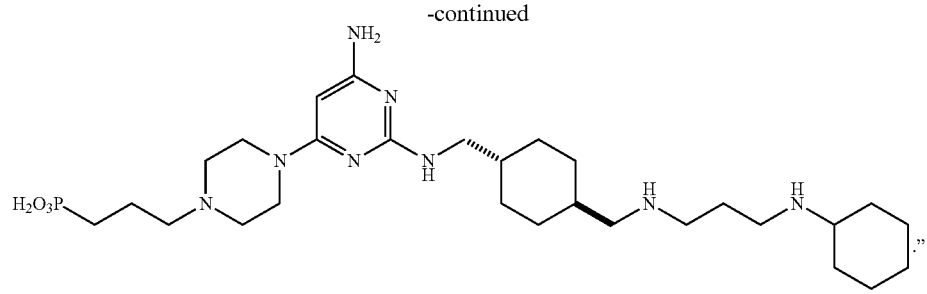
10. The method of claim 9, wherein the compound is:
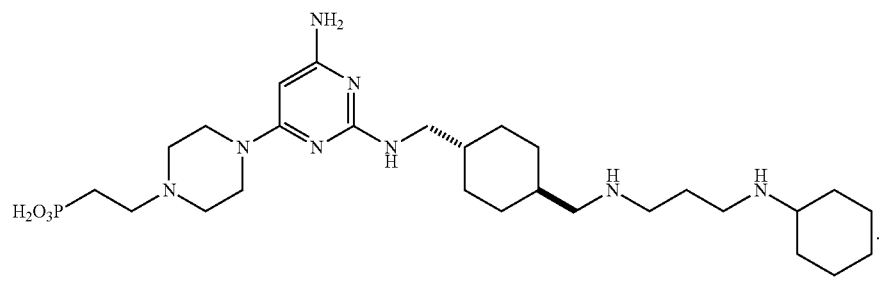
* * * * *